United States Patent
Prieels et al.

(10) Patent No.: US 9,186,525 B2
(45) Date of Patent: Nov. 17, 2015

(54) APPARATUS FOR PARTICLE THERAPY VERIFICATION

(75) Inventors: Damien Prieels, Court-Saint-Etienne (BE); Frédéric Stichelbaut, Mazy (BE); Julien Smeets, Bouge (BE); Alain Dubus, Brussels (BE); Jean-Claude Dehaes, Braine-le-Comte (BE)

(73) Assignees: Ion Beam Applications S.A., Louvain-la-Neuve (BE); Université Libre de Bruxelles, Brussels (BE)

(*) Notice: Subject to any disclaimer, the term of this patent is extended or adjusted under 35 U.S.C. 154(b) by 1 day.

(21) Appl. No.: 13/983,487

(22) PCT Filed: Feb. 3, 2012

(86) PCT No.: PCT/EP2012/051866
§ 371 (c)(1),
(2), (4) Date: Nov. 14, 2013

(87) PCT Pub. No.: WO2012/104416
PCT Pub. Date: Aug. 9, 2012

(65) Prior Publication Data
US 2014/0061493 A1 Mar. 6, 2014

(30) Foreign Application Priority Data

Feb. 4, 2011 (EP) .................................. 11153357

(51) Int. Cl.
*G01T 1/29* (2006.01)
*A61N 5/10* (2006.01)

(52) U.S. Cl.
CPC ............ *A61N 5/1071* (2013.01); *A61N 5/1048* (2013.01); *G01T 1/2914* (2013.01); *A61N 2005/1052* (2013.01); *A61N 2005/1087* (2013.01)

(58) Field of Classification Search
CPC . A61N 5/1048; A61N 5/1031; A61N 5/1071; A61N 5/10; A61N 5/1075; G01T 1/2914
USPC ......................................................... 250/393
See application file for complete search history.

(56) References Cited

U.S. PATENT DOCUMENTS 8,357,907 B2 * 1/2013 Testa et al. ............... 250/370.07
8,481,951 B2   7/2013 Jongen et al.
(Continued)

FOREIGN PATENT DOCUMENTS

| EP | 2140913 A1 * | 1/2010 |
| WO | 2009141570 A1 | 11/2009 |
| WO | 2010/000857 A1 | 1/2010 |

OTHER PUBLICATIONS

Chul Hee Min et al., "Development of an Array-Type Prompt Gamma Detection System for the Online Measurement of the Range of the Proton Beam in a Patient: a Monte Carlo Feasibility Study." Journal of the Korean Physical Society, vol. 52, No. 3, Mar. 2008, pp. 888-891.

Chul-Hee Min et al., "Prompt gamma measurements for locating the dose falloff region in the proton therapy." Applied Physics Letters, vol. 89, 2006, pp. 183517-1-183517-3.

J. Smeets et al., "Prompt gamma imaging with a slit camera for real-time range control in proton therapy." Physics in Medicine and Biology, vol. 57, 2012, pp. 3371-3405.

(Continued)

*Primary Examiner* — Marcus Taningco
(74) *Attorney, Agent, or Firm* — Fitch Even Tabin & Flannery LLP

(57) ABSTRACT

The invention is related to an apparatus and method for charged hadron therapy verification by detecting and/or quantifying prompt gammas produced when irradiating a target (6) with a charged hadron beam. The apparatus comprises a collimator (1) provided with a slit-shaped portion (2) configured to be arranged perpendicularly to the beam line and facing the target, a detection means (3,4) suitable for detecting said prompt gammas and a calculation and representation means. In the apparatus and method of the invention, the slit is configured to allow the passage of prompt gammas emitted from a range of depths in said target (6), said depths being measured in the direction of the charged hadron beam. Furthermore, said detection means is configured to detect prompt gammas emitted from each location within said range, and said calculation and representation means is configured to derive from a detected prompt gamma a value representative of the dose at the location from where said prompt gamma is emitted, and to represent a dose-related distribution for a plurality of locations within said range.

30 Claims, 15 Drawing Sheets

(56) References Cited

U.S. PATENT DOCUMENTS

| | | | |
|---|---|---|---|
| 8,841,602 B2* | 9/2014 | Schulte et al. | 250/252.1 |
| 2008/0237476 A1 | 10/2008 | Uribe et al. | |
| 2010/0012859 A1* | 1/2010 | Claereboudt | 250/492.3 |

OTHER PUBLICATIONS

International Search Report, International Patent Application No. PCT/EP2012/051866, date of the completion Mar. 28, 2012, 3 pages.

* cited by examiner

APPARATUS FOR PARTICLE THERAPY VERIFICATION

CROSS REFERENCE TO RELATED APPLICATIONS

This application is a national phase application of International Application No. PCT/EP2012/051866, filed Feb. 3, 2012, designating the United States and claiming priority to European Patent Application No. 11153357.6, filed Feb. 4, 2011, which is incorporated by reference as if fully rewritten herein.

FIELD OF THE INVENTION

The invention is related to the field of charged Hadron Therapy, i.e. radiation therapy using particles, such as protons or ions (e.g. carbon ions). More particularly, the invention is related to a detection system for measuring the beam range of a charged hadron beam in a target object.

STATE OF THE ART

It is well established that charged hadrons (i.e., protons, pions, ions such as carbon ions) have physical advantages with respect to X-rays or gamma rays in the field of radiation therapy. For example, protons of a given energy (i.e. forming a mono-energetic proton beam), have a certain penetration depth in a target object and do not penetrate beyond that depth, and furthermore, they deposit their maximum amount of energy or dose in the so-called Bragg Peak, which corresponds to said penetration depth, i.e. the point of greatest penetration of the radiation in the target volume. The position of the Bragg peak is also referred as the 'beam range'. Since the Bragg peak position depends on the energy of the hadron beam, it is evident that by precisely controlling and modifying the energy, one can place the Bragg Peak at a given depth of a tumour so as to administer the greatest radiation energy to selected points and spare the healthy tissue surrounding said points.

As a consequence, the location of the Bragg peak must be precisely known since critical tissue localized near the target tumour could receive overdoses, whereas conversely the target tumour could receive underdoses. There is a need therefore to obtain a direct on-line, i.e. during beam delivery, measurement of the particle range.

One option which has been explored is the detection of prompt gammas emitted from a target irradiated by a charged hadron beam. Prompt gammas are emitted isotropically from every location along the charged hadron beam path in the target, so that this path is seen as a gamma line source by a detection apparatus. The detection of said prompt gammas offers a possibility of determining the beam range. One solution of this type is disclosed in the document 'Prompt gamma measurements for locating the dose falloff region in the proton therapy', Chul-Hee Min and Chan Hyeong Kim, 2006 Applied Physics Letters, article 183517. The authors used a gamma scintillation camera equipped with one multilayered collimator system to measure prompt gamma generated by irradiation. Nevertheless, this device is only able to detect prompt gamma emitted from 90° of the beam direction. To obtain the prompt gamma distribution along the beam direction, the detector needs to be moved step by step to different measurement positions which makes this device not useful for practical on-line measurements.

In the document 'Development of an array-type prompt gamma detection system for the on-line measurement of the range of the proton beam in a patient: a Monte Carlo feasibility study', Chul-Hee Min et al, Journal of the Korean Physical Society, Vol 52, N[deg.]3, March 2008, pp 888-891, a linear array of scintillation detectors and photodiodes is disclosed for the online measurement of the proton beam range. This study discloses a collimator with a plurality of slits, for detection of a range of depths in a target. Such a structure is however mechanically complicated. Also, it is feared that such a system cannot offer both a desired spatial resolution and collimation. A good spatial resolution would require a thin shielding but a good collimation would necessitate a thick shielding.

Document WO-A-2010/000857 discloses a system wherein a pin-hole camera is used in conjunction with a scintillator and a 2-dimensional array of photodetectors. Such a system allows to detect the dose fall-off region without requiring a movement of the detectors with respect to the target. The use of pinhole is not regarded as optimal in terms of the number of prompt gammas that are detectable. Further improvement of this type of system is desirable.

AIMS OF THE INVENTION

It is an object of the present invention to provide an apparatus and a method for charged hadron therapy verification which overcomes the drawbacks of prior art detectors and methods.

SUMMARY OF THE INVENTION

The invention is related to an apparatus and method as disclosed in the appended claims. The invention is firstly related to an apparatus for charged hadron therapy verification by detecting and/or quantifying prompt gammas produced when irradiating a target with a charged hadron beam, the beam being directed along a beam line, said apparatus comprising:
- a collimator formed of a first material and provided with a slit-shaped portion which comprises a material of a lower thickness and/or density than said first material, said slit-shaped portion being configured to be arranged perpendicularly to the beam line and facing the target,
- a detection means suitable for detecting said prompt gammas and
- a calculation and representation means, characterized in that:
- the slit is configured to allow the passage of prompt gammas emitted at least from a zone of the target corresponding to a portion of the beam line within said target, said portion of the beam line being larger than the width of the slit-shaped portion,
- said detection means is configured to detect prompt gammas passing through the slit-shaped portion, said prompt gammas being emitted from a plurality of locations within said zone of the target,
- said calculation and representation means is configured to derive from a detected prompt gamma a value representative of the dose at the location from where said prompt gamma is emitted, and to represent a dose-related distribution for said plurality of locations, thereby allowing to estimate the beam range within said target. The latter feature implies that the portion of the beam line from where prompt gammas are allowed to pass through the slit is considerably larger than the width of the slit-shaped portion, for example 5 to 10 times larger.
- said detection means and said calculation and representation means are configured to calculate and represent said value in a plurality of portions of said zone arranged along the beam line, to thereby obtain a one-dimensional view of the dose-related distribution within said zone.

The apparatus of the invention preferably comprises a single collimator provided with a single slit-shaped opening.

According to a preferred embodiment, said detection means comprises a scintillator arranged at a distance from said slit-shaped portion, and having a surface facing said slit-shaped portion, and at least one array of photon counting devices associated with said scintillator.

Said scintillator may be formed of a plurality of segments arranged in a row of segments oriented perpendicularly to the slit-shaped portion.

Alternatively or in addition to the latter embodiment, said scintillator may be formed of a plurality of segments arranged in a row of segments oriented in the direction of the thickness of said scintillator.

Said array of photon counting devices may be arranged parallel to the scintillator. According to another embodiment, said array of photon counting devices is arranged laterally with respect to the scintillator and perpendicularly with respect to the slit-shaped portion.

Said slit-shaped portion may comprise a solid material with a lower thickness and/or density than said first material.

According to a preferred embodiment, said slit-shaped portion extends between the front and back plane of the collimator, said front plane being configured to face the target, and wherein the slit-shaped portion has two side walls, at least one of said two side walls diverging from a given narrower section of the slit to a broader section of the slit situated at the front of the collimator.

According to a further embodiment, the slit-shaped portion comprises a middle portion and two side portions, said side portions being located respectively between the middle portion and said front plane of the collimator, and between the middle portion and said back plane of the collimator, said side portions having diverging walls tapering outwards from the middle portion to the front, respectively the back plane of the collimator.

According to a further embodiment, the middle portion is a throat section having zero length, and wherein the detection means comprises a rectangular face placed at a distance (A) from the central longitudinal axis of the throat section, said face being furthermore symmetrical with respect to the plane through said central longitudinal axis and perpendicular to the plane of the throat section, and wherein the field-of-view angle is defined as the angle between said rectangular face of the detection means and a plane from the central longitudinal axis of the throat section to a side edge of the rectangular face, and wherein the angle between the side walls of the side portion at the front of the collimator and the front plane of the collimator is between 80% and 100% of said field-of-view angle.

According to a preferred embodiment, the width of the middle portion of the slit is between 1 and 10 mm.

Furthermore, the thickness of the collimator may be between 30 mm and 50 mm. The scintillator material may be LYSO or LSO. The collimator material may be tungsten or a tungsten alloy.

Said scintillator and said array of photon counting devices may be mounted inside a housing which is fixed with respect to the collimator.

According to an embodiment, the apparatus is configured to be movable with respect to the target. According to a further embodiment, the apparatus comprises a holder onto which the apparatus is mounted and a robotic arm onto which the holder is mounted.

The invention is also related to a method for charged hadron therapy verification by detecting and/or quantifying prompt gammas produced when irradiating a target with a charged hadron beam, said beam being directed along a beam line, comprising the steps of:
arranging adjacent to a target a collimator with a longitudinal slit shaped portion, said slit-shaped portion being configured to be arranged perpendicularly to the beam line and facing the target, said slit-shaped portion being configured to allow the passage of prompt gammas emitted at least from a zone of the target corresponding to a portion of the beam line within said target, said portion of the beam line being larger than the width of the slit-shaped portion,
irradiating said target with a charged hadron beam directed along said beam line,
detecting prompt gammas emitted from a plurality of locations within said zone of the target, said prompt gammas passing through said slit-shaped portion,
deriving from said detected prompt gamma a 1-dimensional dose-related distribution for said plurality of locations.

The method may further comprise the step of estimating the beam range on the basis of said distribution.

According to a preferred embodiment, a window of energy levels for prompt gammas is defined, and wherein only prompt gammas are detected within said energy window. Said energy window may be between 3 MeV and 7 MeV, more preferably between 3 MeV and 6 MeV.

According to an embodiment of the method, said 1D distribution is approximated by a 3-line segment curve.

The method may further comprise the step of estimating a shift in the beam range by subsequently obtaining said 1D distribution several times, and by determining the shift of the 3-line segment curves associated with the obtained 1D distributions.

In each of the above described embodiments, the collimator may have the form of a flat panel provided with a longitudinal slit shaped portion. In this case, the scintillator is also flat shaped and facing the longitudinal slit-shaped portion. In another embodiment, the collimator is cylindrically shaped, and configured to be placed around a target. In this case, the slit-shaped portion extends along a circular circumference of the collimator. In the latter embodiment, the scintillator may also be cylindrically shaped and placed around the collimator.

BRIEF DESCRIPTION OF THE FIGURES

FIG. 1a shows a schematic view of an apparatus according to the invention, involving a collimator having a longitudinal slit. FIG. 1b is a section view of the plane A-A' of FIG. 1a. FIG. 1c is a section view of the plane B-B' of FIG. 1a.

DETAILED DESCRIPTION OF THE INVENTION

Figure 1:
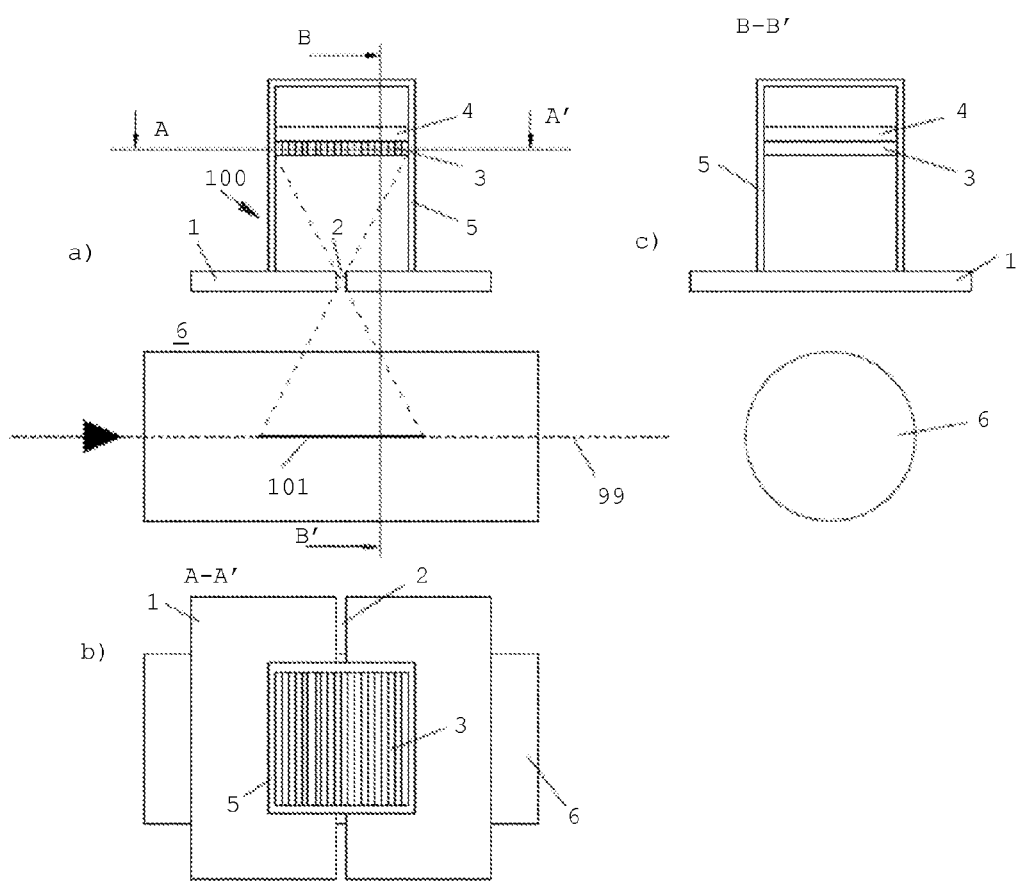

FIG. 1 shows an embodiment of an apparatus of the invention. The apparatus 100 comprises a collimator 1 with a longitudinal slit-shaped opening 2. In use, the system is mounted next to a target, e.g. a cylindrical water target 6, on which a charged hadron beam, e.g. a proton beam impinges in the direction of the arrow, and follows a path defined by the beam line 99 (i.e. the beam line 99 is a mathematical representation of the path the beam would follow if no target were present). The slit 2 is oriented perpendicularly to the beam line. At a distance from the collimator, a scintillator 3 is placed, arranged in association with an array 4 of photon counting devices. As known in the art, the scintillator comprises a scintillating crystal material which is capable of interacting with prompt gammas emitted from the target, said interactions generating the emission of photons, which are detected by the devices in array 4. The scintillator has a flat shape parallel to the beam direction, e.g. a rectangular or square shape as shown in the drawing, so that one flat surface of the scintillator faces the longitudinal slit 2 at a predefined distance from said slit.

The thickness of the collimator and the shape of the slit as seen in cross-section taken perpendicularly to the longitudinal axis of the slit, is such that prompt gammas emitted from a zone of the target corresponding to portion 101 of the beam line may enter through the slit 2 and be projected onto the scintillator. Said portion 101 may be referred to as the visible field of view of the apparatus. As can be seen in the drawing, the visible field of view 101 is considerably larger than the width of the slit-shaped portion 2, i.e. the apparatus of the invention allows to detect prompt gamma emitted not only from the direction which is at 90° with respect to the beam direction. The visible field of view may be equal to or smaller than the length of the beam line within the target.

The longitudinal form of the slit-shaped portion is advantageous in that it allows a 1-dimensional view of the photon count in the field of view. During data treatment, events are selected belonging to energy windows (for example between 3 MeV and 6 MeV), corresponding to prompt gammas and these events are integrated in bins (of typically 5 mm width) along the beam axis. As a result, a 1D projected image is obtained along the beam axis of the proton beam path inside the target with reasonable statistics and spatial resolution, without moving the detector (which overcomes drawbacks of prior methods). Said 1D image is called the detection profile, i.e. a one-dimensional view of the dose-related distribution within the field of view.

Figure 1D:
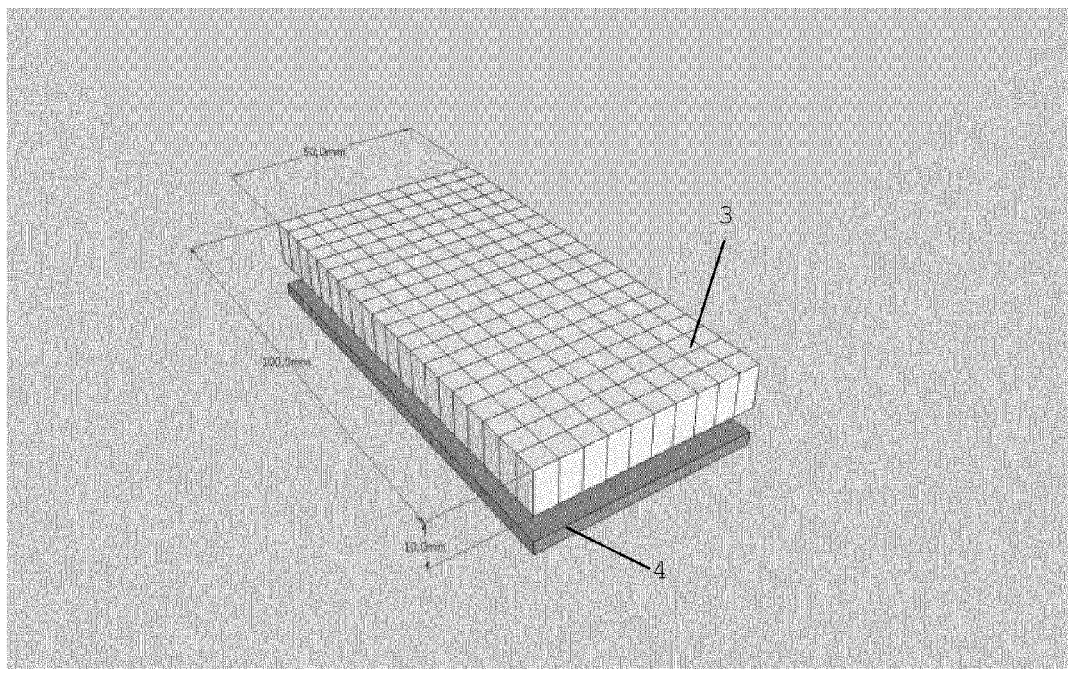
FIG. 1d is a 3-D view of a scintillator and detector array, the scintillator comprising a 2-dimensional array of scintillator segments.

The detected field of view is determined by the width of the scintillator 3 in the direction parallel with the beam. Preferably but not necessarily, the detected field of view is equal to the visible field of view. According to a preferred embodiment, the scintillator is divided in segments arranged side by side in said direction parallel to the beam (i.e. the segments themselves are perpendicular to the beam direction), so that prompt gammas are detected in each segment individually, each segment corresponding with a portion of e.g. 5 mm within the field of view. In other words, an 1-dimensional array of scintillator segments is provided, as shown in FIGS. 1a and 1b. The scintillator may also be formed of a 2-dimensional array of scintillator segments, see FIG. 1d.

The integration in each 5 mm-portion may be done by applying the segmented scintillator of FIG. 1, wherein the events in each segment are integrated to yield a photon count for each 5 mm-wide portion along the beam axis (i.e. a 1-dimensional graph). Alternatively, the scintillator may be uniform instead of segmented, and the integration is done purely on the basis of the output of the photon counting devices (when a 2-D array of photon counting devices is present).

The array 4 of photon counting devices can be an array of photomultiplier tubes or other detector means known in the art, e.g. Silicon drift detectors (SDD) or Silicon avalanche photodiodes (Si APD). The array of photon counting devices is used to determine both energy and position of energy deposition events occurring in the scintillator. In the embodiment shown, the array 4 is a two-dimensional array of detectors, placed in a plane parallel to the plane of the scintillator. An alternative to this arrangement will be described further in this text.

The projection of the field of view can be obtained for a variety of slit shapes as seen in cross section perpendicular to the longitudinal slit direction. It can be obtained with a slit having parallel side walls as shown in FIG. 1, provided that the collimator thickness is sufficiently low with respect to the width of the slit. According to preferred embodiments, the slit has a conical shape, as described further in more detail with reference to FIGS. 3 and 7.

A housing 5 encloses the area between the scintillator 3 and the collimator 1, wherein the housing comprises the detector array and the scintillator and the housing is fixed with respect to the collimator. The housing may be produced from the same material as the collimator. The housing may form a single body with the collimator. Any embodiment involving such a housing 5 may also be called a prompt gamma camera. However, the apparatus of the invention may also be provided without a housing 5.

As stated, a selection is preferably made of the energy of the detected particles emitted from the target, within a given energy window. This is done to select unscattered high energy prompt gammas and exclude, as much as possible, neutrons and low energy scattered gammas. According to a preferred embodiment, only prompt gammas with energy between 3 and 6 MeV are selected. A suitable means (as known in the art) is provided in the apparatus for performing said selection. The apparatus further comprises suitable calculation and representation means (not shown) to derive from the detected prompt-gamma a dose-related distribution (preferably the photon count), and to represent said distribution in the form of a 1-dimensional view, as a function of the position in the field of view 101 in the beam direction, e.g. a graph on a display (see e.g. FIG. 10, described in more detail further in this text). From this graph, the position of the Bragg peak can be determined. The apparatus may further comprise a means for executing a time-of-flight calculation on the detected events, and to correct the photon count on the basis of said calculation, as described in document WO2009/141570, incorporated herein by reference.

Figure 2A:
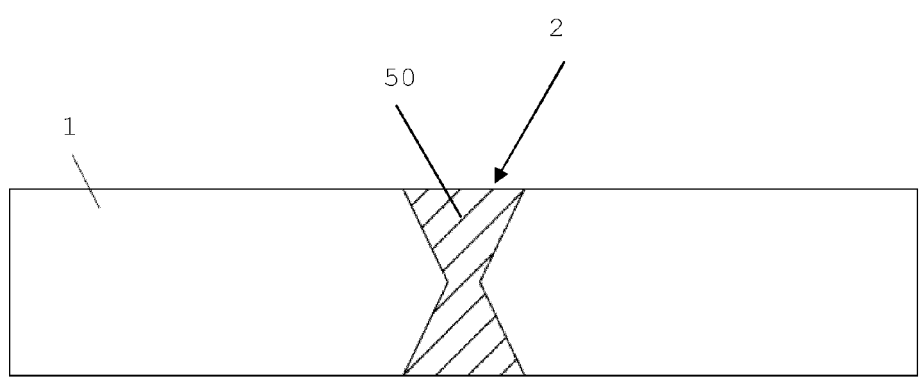
FIGS. 2a to 2d show a number of embodiments wherein the slit shaped portion comprises a solid material.
Figure 2B:
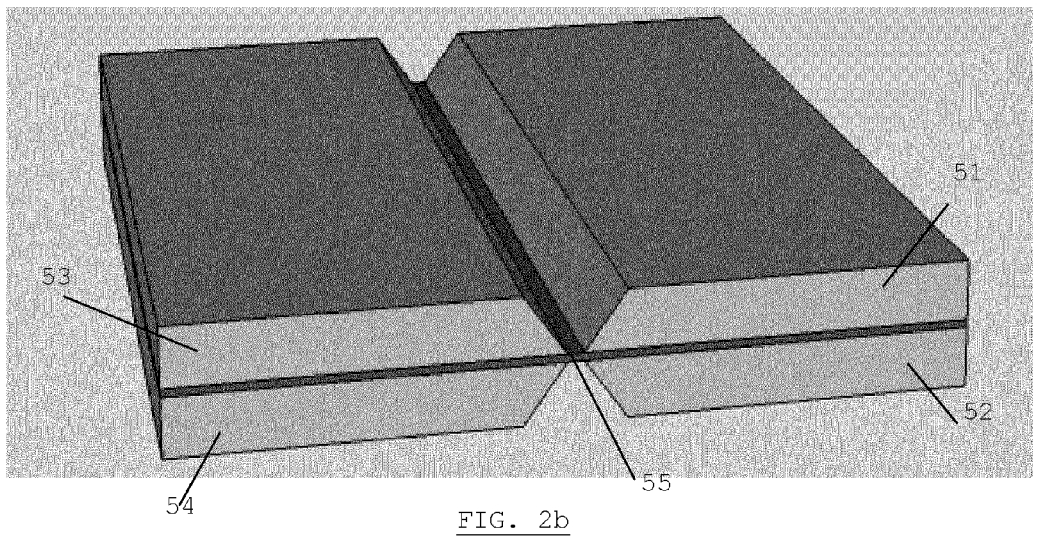
Figure 2C:
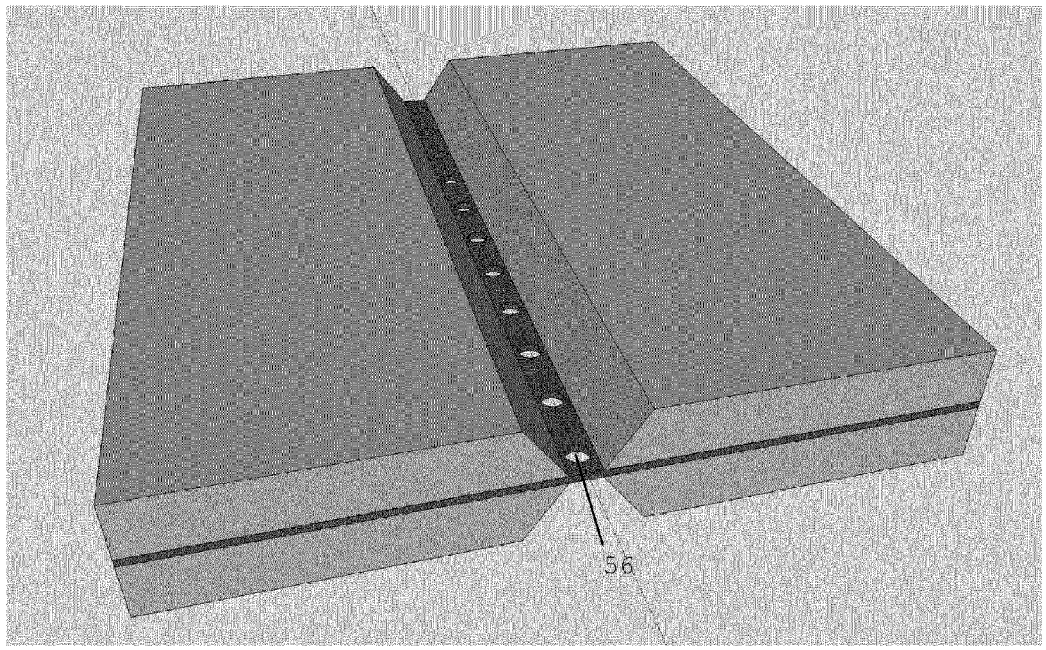
Figure 2D:
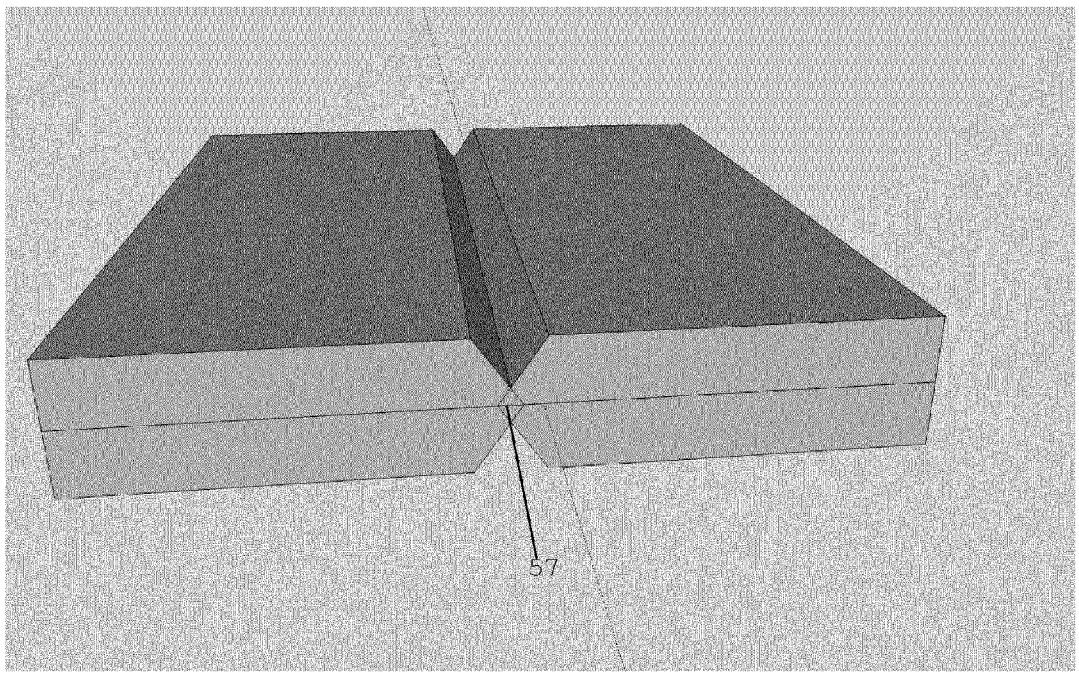

The slit 2 can be open (i.e. filled with ambient, mostly air), or it can comprise or consist of a material with a thickness and/or a density which is lower than that of the collimator material. Some examples of such a collimator are shown in FIGS. 2a-2d. FIG. 2a shows an embodiment wherein the slit-shaped opening is filled with a plastic material 50 of lower density than the collimator material, which is produced e.g. from Tungsten. FIG. 2b shows an embodiment, wherein the collimator is formed of four parts 51 to 54, e.g. in tungsten, placed symmetrically 2 by 2 with respect to a central plate 55 of e.g. lead, so that the slit-shaped portion is formed of a strip of lead between the side walls of the collimator portions. Openings 56 may be provided in the centre plate, see FIG. 2c. Another possibility is a collimator with a longitudinal portion 57 which is thinner than the bulk of the collimator, e.g. by the removal of two longitudinal portions of triangular section (see FIG. 2d). The width of the slit-shaped portion 2 is defined as the width of the area which has a smaller thickness and/or density than the body of the collimator.

As shown already in some of the described embodiments, the slit-shaped portion may have a conical or at least partially conical cross-section. Preferably, this means that at least one longitudinal side wall of the slit-shaped portion diverges from a given narrower section of the slit to a broader section of the slit situated at the front of the collimator, i.e. the side which faces the target. When the narrow section is located between the front and back plane of the collimator, at least one of the walls between the narrow section and the back of the collimator equally diverges from said narrow section towards a broader section situated at said back plane of the collimator.

Figure 3A:
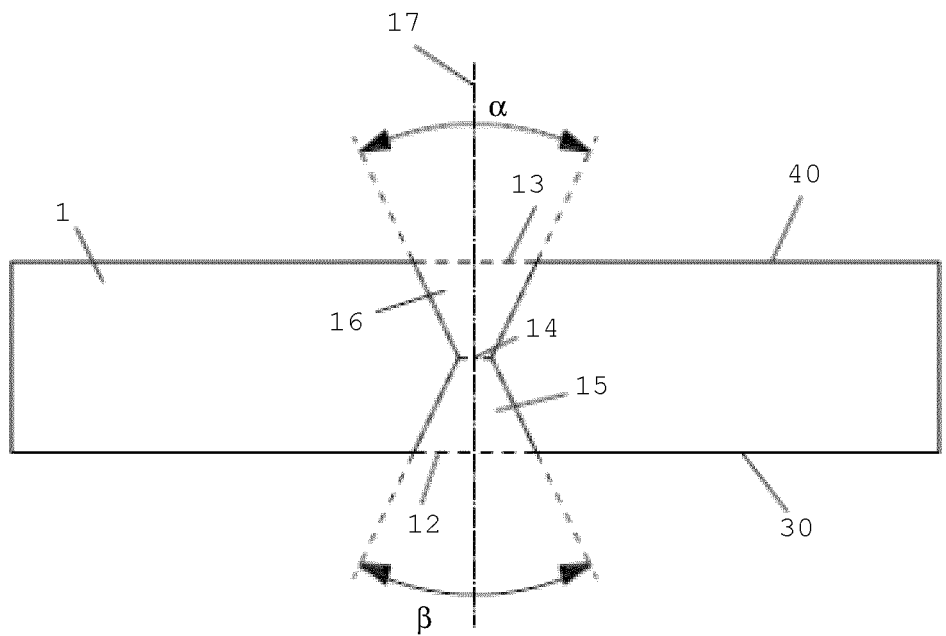
FIGS. 3a and 3b illustrate preferred embodiments of a slit with a double conical shape.
Figure 3B:
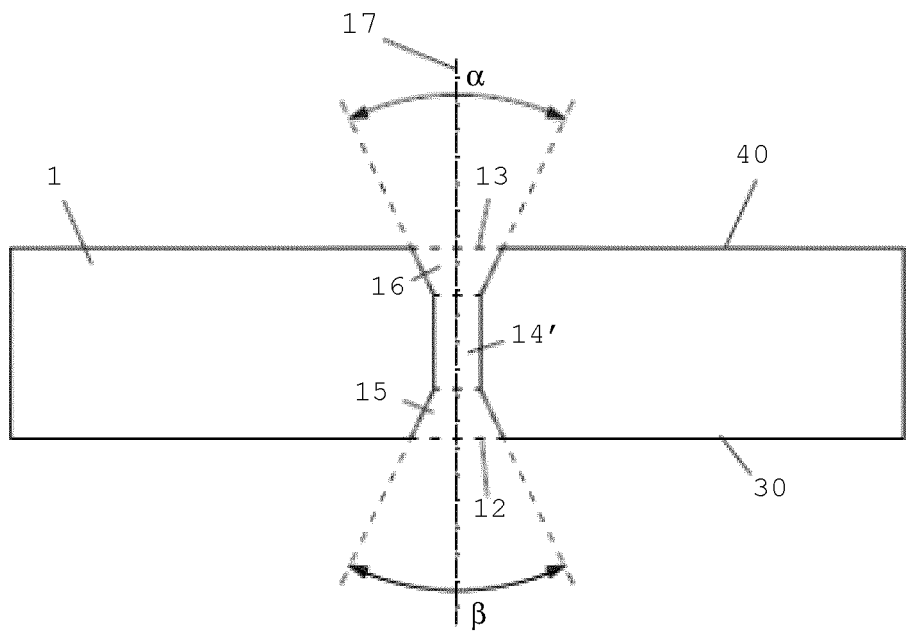

In the preferred embodiment, the slit shape is a double conical shape as shown in FIGS. 3a and 3b, wherein the slit shape is defined by a first broad section 12 at the front plane 30 of the collimator, i.e. the plane which faces the target, a second broad section 13 at the back plane 40 of the collimator, and a central narrow portion 14 or 14', with tapered portions 15 and 16 between the front and back sections and the central section respectively. The tapered portions are symmetrical with respect to the slit's centre line 17 which runs perpendicularly to the collimator. Preferably the narrow section 14 is situated half-way between the front and back sections 12 and 13. The narrow section 14 can be a throat section with zero length in the direction perpendicular to the collimator, as shown in the embodiment of FIG. 2a or it may be a channel section 14' arranged centrally between the two tapered sections 15 and 16, as shown in FIG. 3b. Preferably, the angles α and β of the tapered sections are equal to each other.

Figure 4:
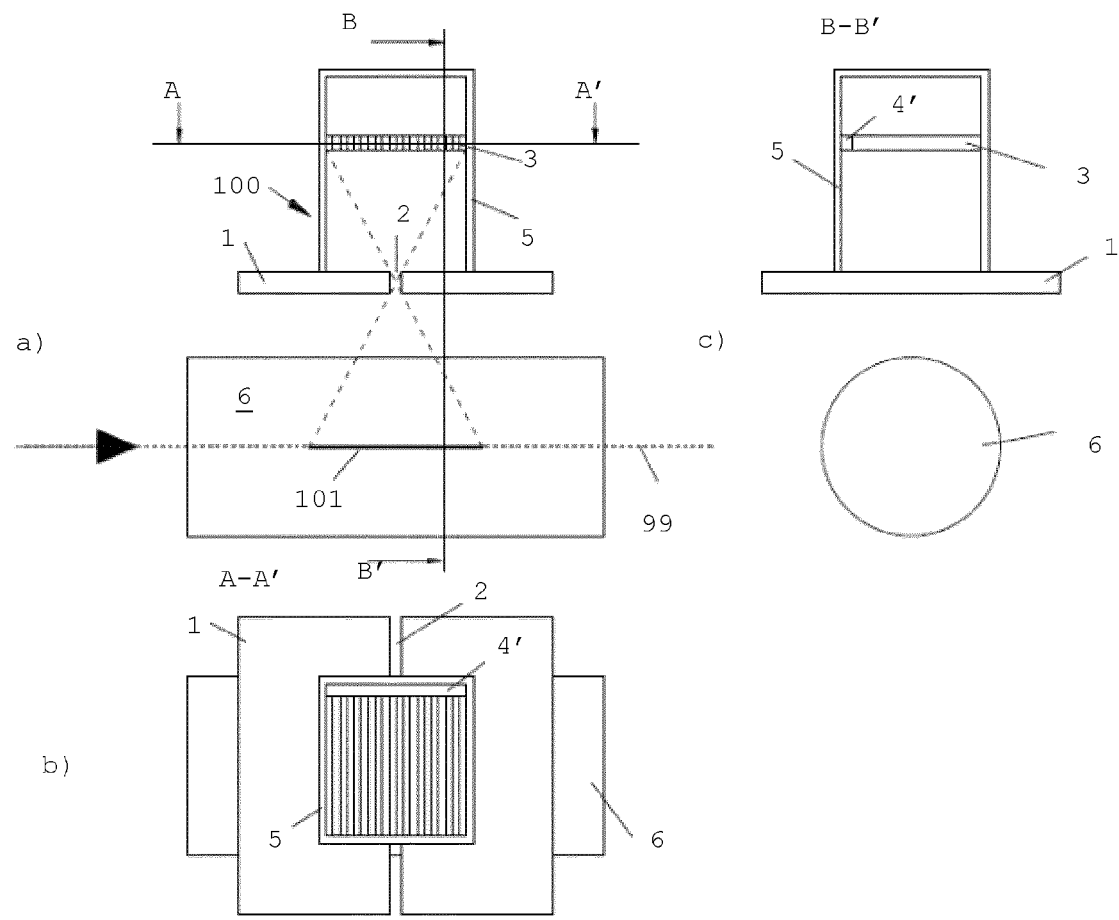
FIGS. 4a-4c shows an alternative embodiment in terms of the position of the photon counting devices with respect to the scintillator. The views are arranged in the same way as in FIGS. 1a-1c.
Figure 5A:
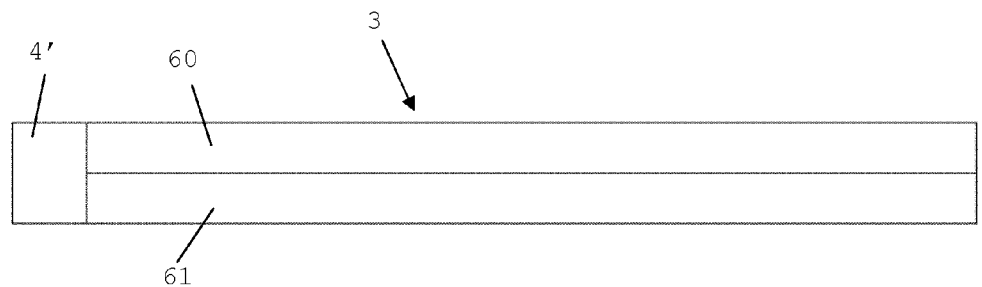
FIGS. 5a and 5b illustrate a preferred embodiment of the alternative of FIG. 4.
Figure 5B:
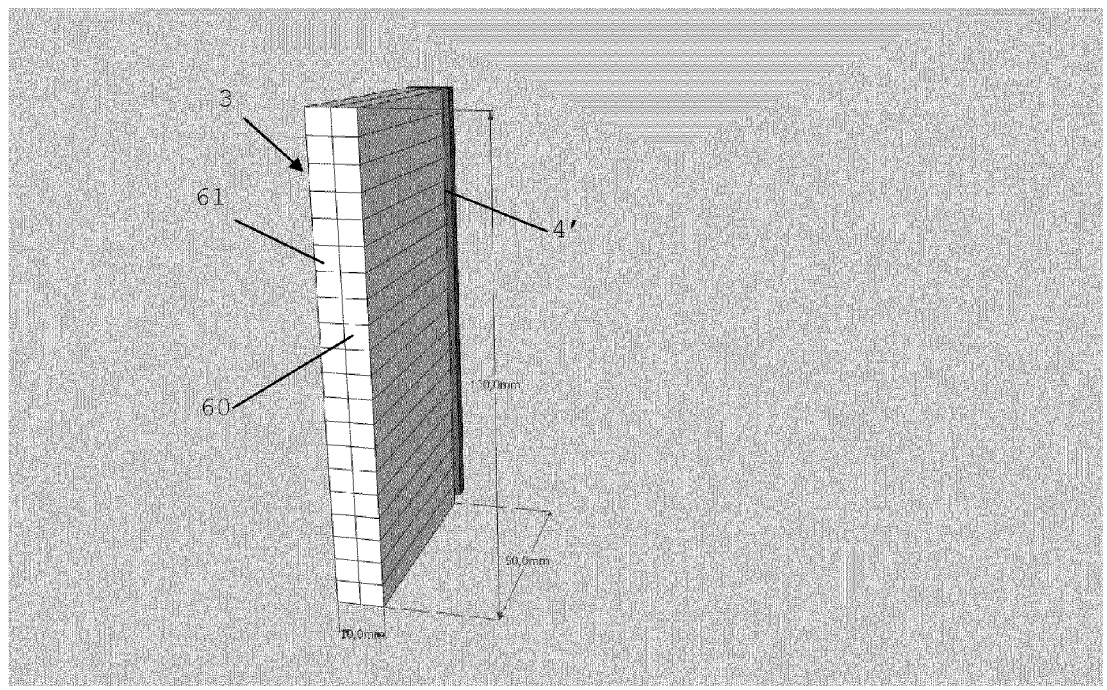

According to an embodiment, the array 4 of photon detectors is not placed parallel to the plane of the scintillator 3, but it is placed laterally with respect to the scintillator, preferably parallel to one or two side edges of the scintillator, and at the same time perpendicular to the slit 2. This version is illustrated in FIG. 4 where the array of photon detectors is indicated by numeral 4'. This embodiment does not allow a 2-dimensional view in the plane of the scintillator, but it does allow the 1-dimensional view. According to a particularly useful embodiment, this orientation of the array 4' can be combined with a scintillator which is segmented in its thickness direction and possibly also in the direction of the beam, see FIGS. 5a and 5b. Generally, the thicker the scintillator, the higher the number of interactions taking place within the crystal, and thus the higher the photon count. However, a thicker scintillator also creates a parallax error on the prompt gamma detection, as no distinction can be made between interactions taking place at different positions in the direction of the scintillator thickness. By providing a segmented scintillator in the thickness direction, in combination with a photon detector array in the direction perpendicular to the slit, this problem can be solved. FIG. 5a/5b illustrates the case wherein the scintillator is divided in two equal segments (layers) 60 and 61, so that the array 4' is capable of detecting a one-dimensional view of the photon count in both of said layers 60 and 61. Each layer will produce a different 1-dimensional view, each identifying a slightly different location of the Bragg peak.

Figure 6A:
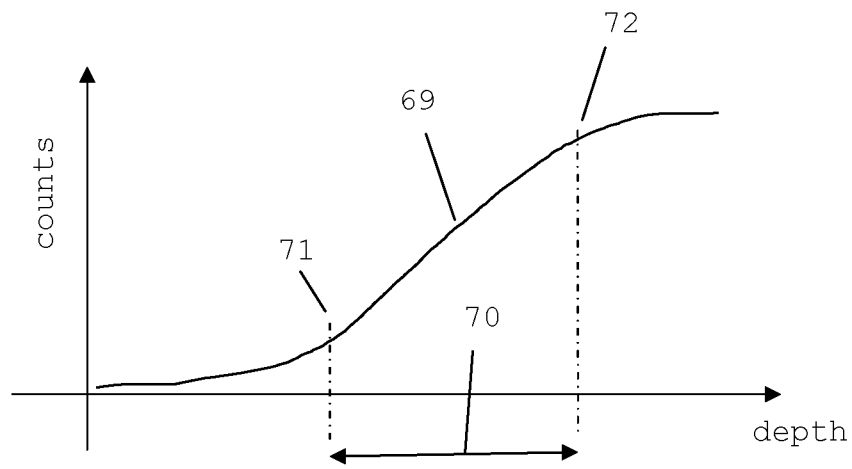
FIGS. 6a and 6b illustrate how the embodiment of FIG. 5 can lead to a more accurate estimation of the beam range.
Figure 6B:
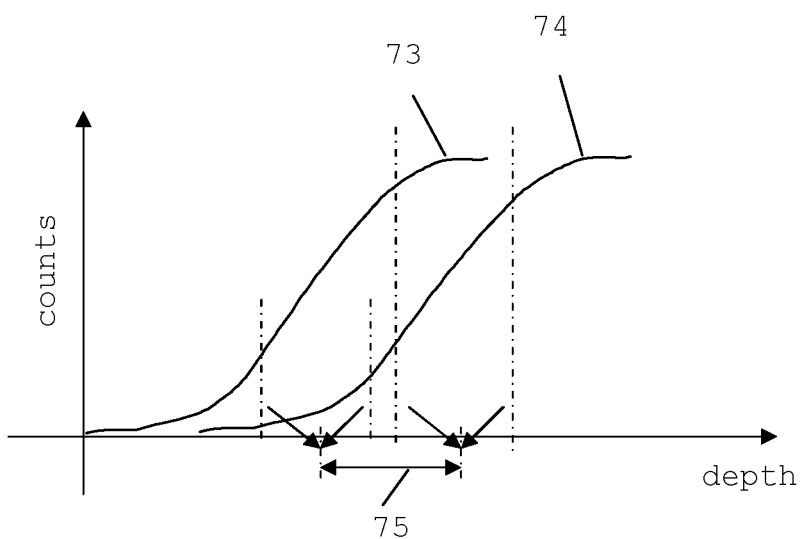

This is illustrated in more detail in the graphs of FIGS. 6a and 6b, which are showing graphs of the number of photon counts as a function of the penetration depth of the hadron beam in the target. When a single scintillator layer is used, (FIG. 6a) the beam range (i.e. location of the Bragg peak) is estimated to correspond to a value within a given zone 70 in which the number of registered counts, as represented by curve 69, is seen to rise. The zone 70 is defined by a low and high threshold (lines 71, 72). When the scintillator is divided in two layers, 2 curves 73 and 74 are obtained, as seen in FIG. 6b. Each curve is sharper than the original one and the sum of the 2 curves should give back the original curve. However, the additional information obtained from these 2 curves allows a more precise determination of the actual range of the proton beam. By averaging the low and high thresholds of the 2 curves, a more narrow estimation zone 75 is obtained for the location of the Bragg peak.

By increasing the number of the layers 60/61 to more than 2, this accuracy can be further increased. This embodiment therefore allows to increase the thickness of the scintillator, thus increasing the number of detected interactions, whilst ensuring an optimal accuracy of the determination of the Bragg peak.

Figure 7:
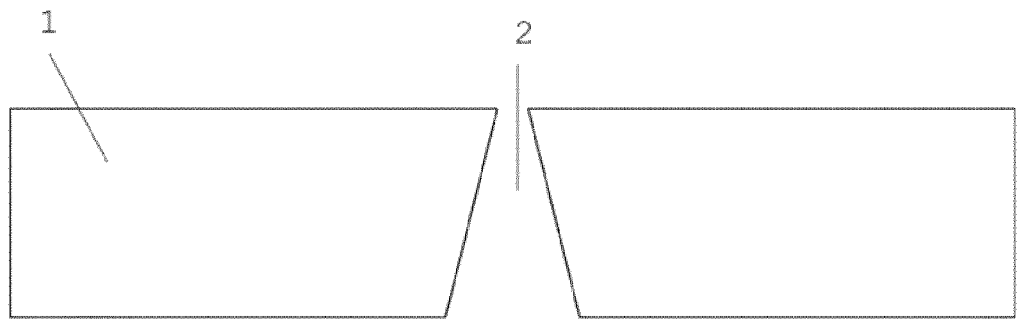
FIG. 7 shows a number of alternative embodiments of the slit shape.
Figure 7:
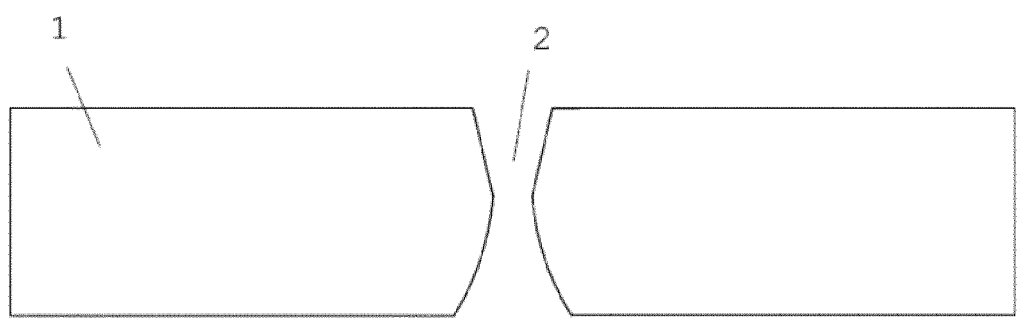
Figure 7:
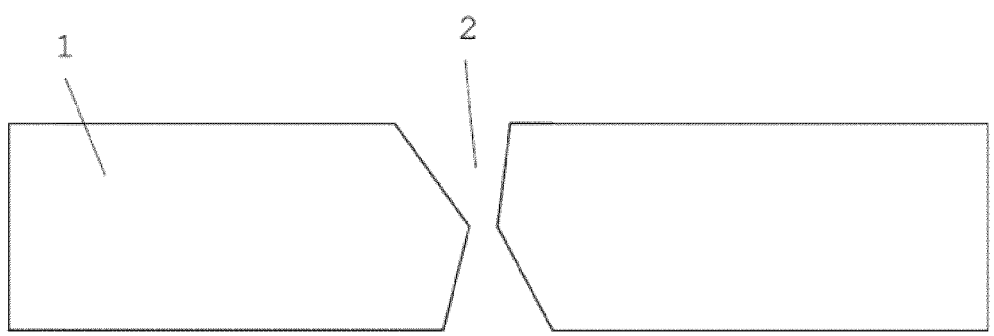

FIG. 7 shows a number of slit shapes that also fall within the scope of the present invention.

According to a particular embodiment, the apparatus of the invention may be configured to be movable with respect to the target. In the latter case, the apparatus 100 as shown in FIG. 1 or 4, i.e. including the collimator, scintillator and detector array, is then movable, preferably in the direction parallel to the beam direction. In this manner, a larger area (meaning larger than the visible field of view) of the target can be verified by obtaining subsequent images of the target at different positions along the beam axis. In practice, the apparatus may be provided with a holder onto which the apparatus is mounted, said holder being itself mounted on a rail or a robotic arm, depending on the number of degrees of freedom of the required movement. The preferred embodiment is a system wherein the apparatus can move freely around the target, in order to take up the best possible position with respect to the target, and in addition to be able to move linearly in the direction of the beam.

The apparatus may be provided with two arrays of photon counting devices parallel to the scintillator, one to each side of the scintillator. This allows to calculate the position of the interaction along the crystal thickness, and as a result to obtain a good spatial resolution with a thicker scintillator.

Figure 8:
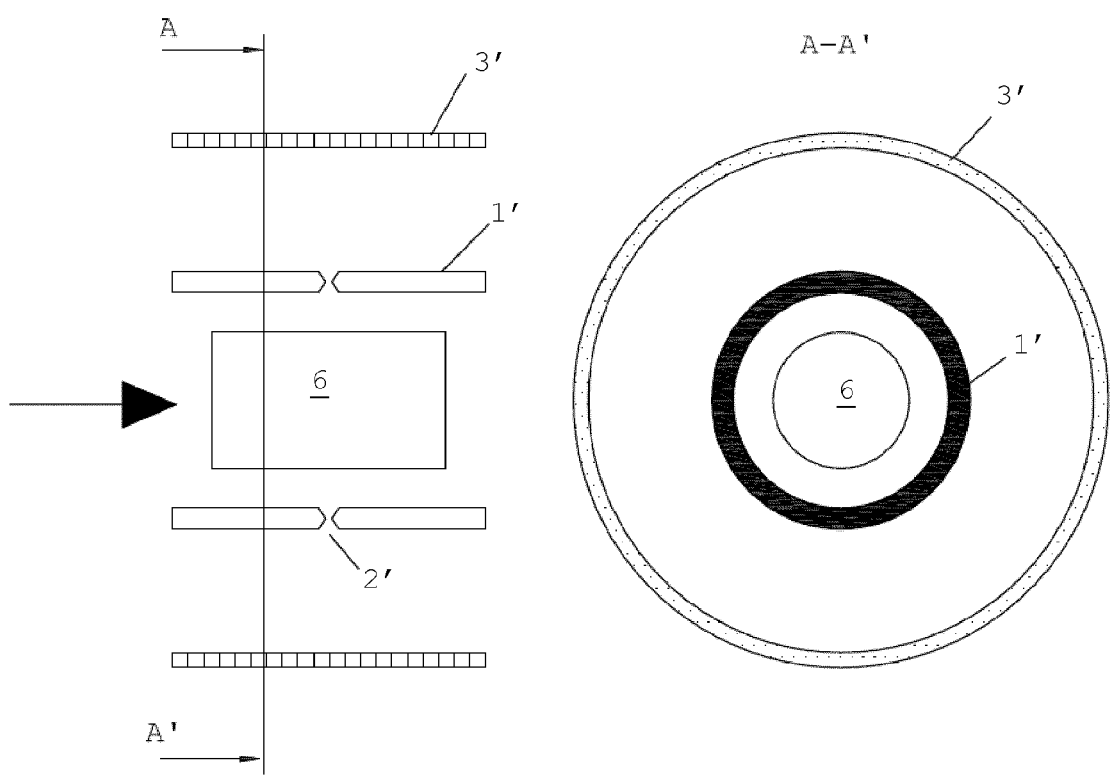
FIG. 8 shows an alternative set-up with a cylindrically shaped collimator and scintillator placed around a target.

The invention is not limited to the embodiment wherein the collimator and detection means are located to one side of the target. FIG. 8 shows an embodiment wherein the collimator 1' and scintillator 3' are cylindrically shaped, and arranged all around a cylindrical water target 6. The slit-shaped portion 2' is now circular instead of longitudinal. The array of photon counting devices could be placed in an additional cylindrical layer around the scintillator 3'.

A number of parameters have been optimized in the embodiment of FIG. 1, but wherein the slit 2 has a double conical shape as shown in FIG. 3a, and an array 4 of detectors parallel to the plane of the scintillator. These parameters are summarized hereafter:

Shape of the Slit

Figure 9:
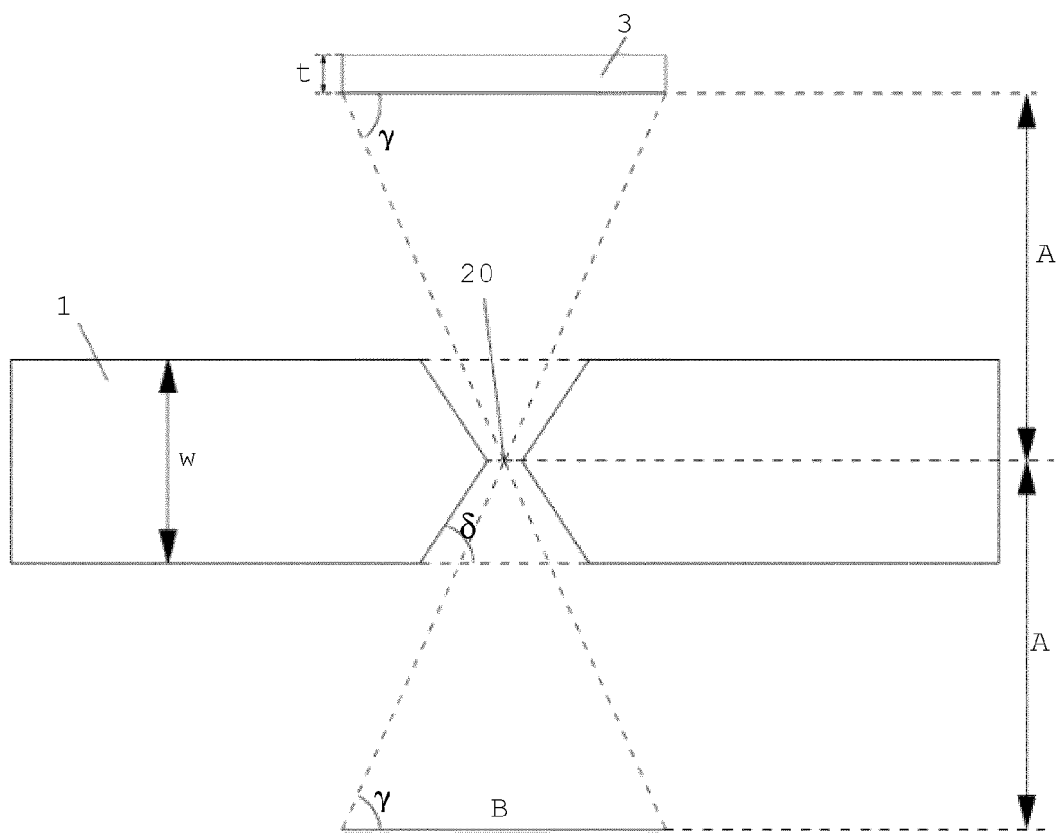
FIG. 9 shows the field of view of an apparatus according to the invention, and a preferred geometry of the slit with regard to said field of view.

FIG. 9 again shows the preferred configuration of the apparatus of the invention, with a preferred shape of the slit, having a throat section 14 and symmetrical tapered portions 15 and 16. The angle δ defines the slope of the tapered portions. The scintillator is square shaped and faces the collimator symmetrically with respect to the slit, i.e. the scintillator is symmetrical with respect to the plane through the central longitudinal axis 20 of the throat section and perpendicular to the plane of the throat section. The field of view of the scintillator through the slit is defined as the line B as viewed from the centre line 20 of the throat section, the line B having the same width as the width of the scintillator 3 and placed at the same distance A as the distance from the scintillator 3 to the centre line 20. For example, when A=15 cm and B=10 cm, γ equals 71.6°. This is the geometrical angle corresponding to the field of view. Simulations were done of detected prompt gamma with a cylindrical water target (diameter 10 cm) of which the central axis was placed at 15 cm from the throat section, the throat section having a width of 1 mm, a square shaped scintillator with a width of 10 cm being positioned at 15 cm on the opposite side. Various angles δ were simulated. From these simulations, it was found that the optimal value of the angle δ in terms of the detection of the Bragg peak was 63°, i.e. about 88% of the geometrical angle. In general, the angle δ is preferably between 80% and 100% of the geometrical field-of-view angle γ.

Width of the Slit

The preferred width of the slit (defined here as the width of the throat section 14 or 14') is between 1 and 10 mm, typically 6 mm. At values above 10 mm, spatial resolution deteriorates.

Collimator Material and Thickness w

The collimator is preferably made from Tungsten or a Tungsten alloy or an (alloy of) equivalent high density metal, such as tantalum. The preferred thickness of the collimator is between 30 mm and 50 mm, most preferably 40 mm. At a lower thickness, the detection profile of photons deteriorates. Above the 30-50 mm range, no sufficient improvement in terms of the detection profile is observed.

Scintillator Material and Thickness

According to one embodiment, the scintillator material is $Bi_4Ge_3O_{12}$ (BGO). According to a more preferred embodiment, the scintillator material is $Lu_{1.8}Y_{0.2}SiO_5$ (LYSO) or the very similar $Lu_2SiO_5$ (LSO). LYSO has a shorter decay time and a better light output than BGO. The thickness of the scintillator may for example be around 10 mm.

Example with Optimized Parameters

Figure 10:
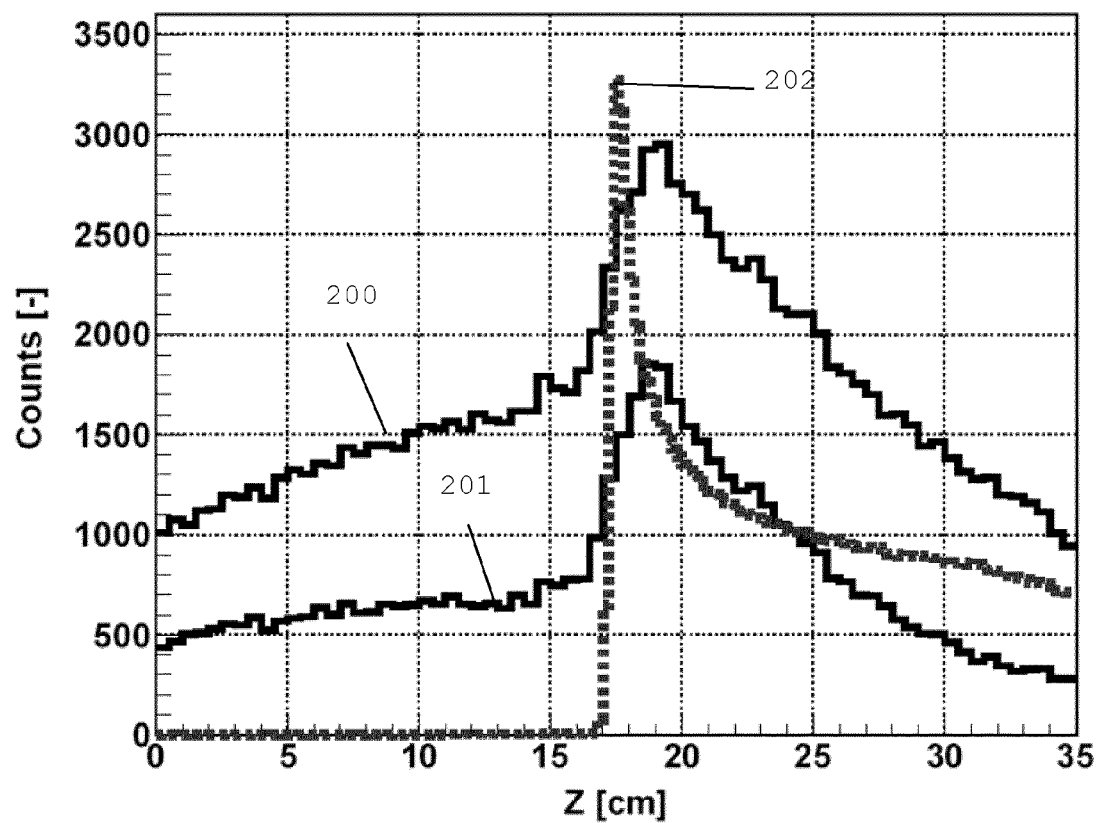
FIG. 10 shows a 1-dimensional graph of the photon count in the investigated field of view within a target, obtainable with an apparatus of the invention.

FIG. 10 shows the photon count obtainable with an apparatus of the invention, in a set-up with a double conical slit shape, and the further set-up of FIG. 1, and further with the following parameter values:

TABLE 1

| Parameter | Value |
| --- | --- |
| Collimator thickness | 40 mm |
| Collimator material | Tungsten alloy |
| Slit angle | 63.4° |
| Slit width | 6 mm |

TABLE 1-continued

| Parameter | Value |
| --- | --- |
| Scintillator thickness | 10 mm |
| Scintillator material | LYSO |
| Pixel size (i.e. scintillator segment width) | 5 mm |
| Energy window | 3-7 MeV |

Curve 200 is the total number of counts detected in the field of view in the Z-direction, which is the direction of the beam, for a proton beam of 160 MeV (pencil beam with a Gaussian profile of 5 mm sigma at target entrance). Curve 201 is the number of counts due to photons within the energy range of 3-7 MeV. The difference is due to the fact that besides prompt gamma (which are photons), secondary emissions from the target (mainly neutrons) can be detected which are not clearly correlated with the beam range. As stated, prompt gammas are emitted isotropically along the proton beam path in the target so that this path is seen as a gamma line source by the apparatus. Neutrons are also emitted, but not isotropically, and they are not efficiently selected by the collimator, so that neutrons detected do not help to determine the beam range. The curve 202 is a projection of the Bragg peak position. It is clear that the photon count curve 201 offers an accurate estimation of the Bragg peak location.

Method for Estimating Beam Range Shifts

Figure 11:
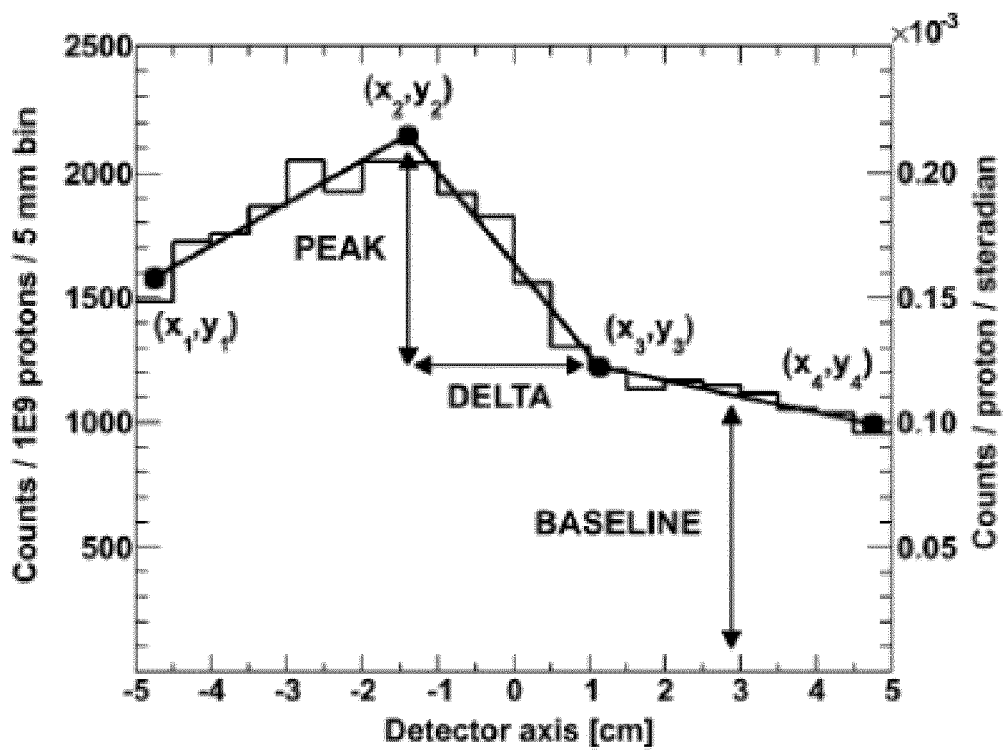
FIG. 11 illustrates how a detection profile obtained by an apparatus and by the method of the invention is approximated by a 3-line segment curve.

The invention is equally related to a method for estimating shifts (i.e. changes) in the beam range on the basis of measurements performed with an apparatus according to the invention. In a first step, the detection profile is represented by a 3-line segment fit, as illustrated in FIG. 11. The detection profile is the reversed 1D projection on the scintillator of the proton track through the slit. The stepped curve 300 in FIG. 11 shows the photon count per 5 mm-wide scintillator segment, as a function of the position along the target axis. The zero-position corresponds to the Bragg peak location. The selected fit is a curve composed of 3 line segments defined by 4 points $(x_i, y_i)$ (i=1 . . . 4) where the abscissa x is the depth along the beam axis and the ordinate y is the number of photon counts. The value $x_1$ is set to the centre of the first 5 mm-wide segment of the scintillator, and $x_4$ is set to the centre of the last segment. The 6 remaining coordinates of the 4 knots are selected to minimize the root mean square (RMS) error. Every fit is characterized by 4 values: the baseline calculated as $(y_3+y_4)/2$, the peak defined as $y_3-y_2$, the delta evaluated as $x_3-x_2$ and the RMS error of the fit.

Figure 12:
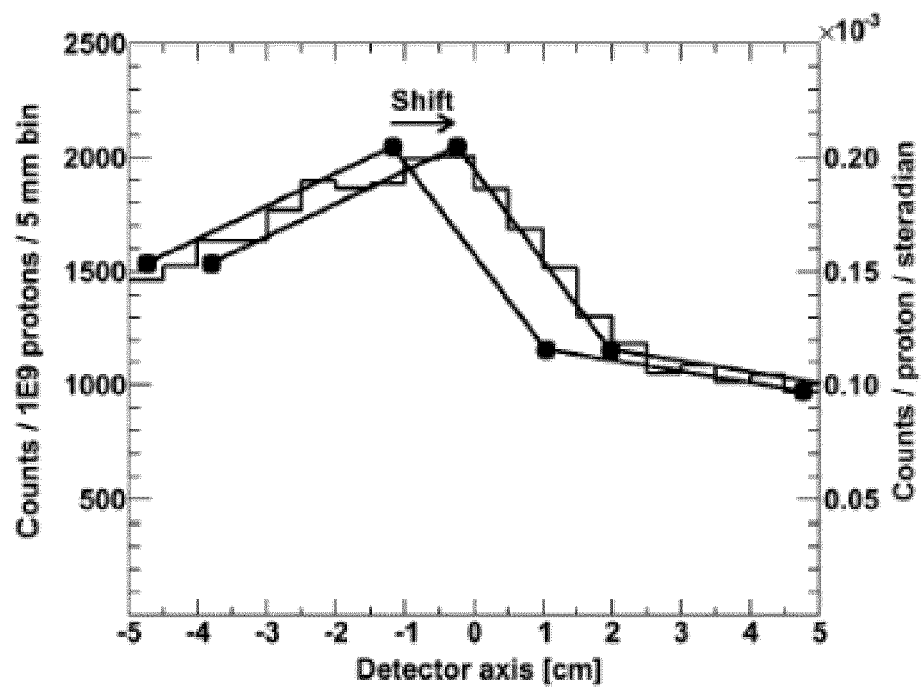
FIG. 12 illustrates how a beam range shift can be determined on the basis of a shift of the 3-line segment curve.

When a shift in the beam range occurs, this shift is detected by the shift of the 3-line segment fit, as illustrated in FIG. 12. Tests have shown that this shift detection method can be performed with an accuracy in the order of 1-2 mm for proton pencil beams of 100 MeV and 160 MeV. This means that changes in the position of the Bragg peak of this magnitude can be detected with an apparatus according to the invention. It was found also that the measured 3-line segment curves on a PMMA target or a water phantom target correspond very well with simulated curves in terms of the delta and peak values, except for a shift in the baseline value (vertical position of the curves). By shifting the measured curves vertically in the graph until they correspond to the simulated curves, the range shift can be measured with respect to the simulated curve. This means that a slit camera according to the invention can be calibrated with simulated data. Simulations can be made with tools that are known to the skilled person (e.g. Monte Carlo simulations).

Experiments and Prototype

A prototype was built reproducing the simulated reference setup of FIG. 1 with the optimized parameters of table 1 (except for the energy window that was chosen as 3-6 MeV in the experiments). Proton pencil beams of 100 and 160 MeV were incident along the axis of a cylindrical PMMA target (7.5 cm radius and 20 cm length). A HiCam detection system (High resolution camera as described in 'Silicon drift detector arrays for the HICAM gamma camera, Fiorini et al, 2008 IEEE Nuclear Science Symp. Conf Record (NSS) 2981-3 and 'The HiCam Gamma Camera', Peloso et al, 2010 IEEE Nuclear Science Symp. Conf. Record (NSS/MIC)1957-60) was placed at 30 cm distance, corresponding to the entrance of the 1 cm thick LYSO scintillator (Saint-Gobain) preceded by a 2 mm thick aluminium sheet. The standard HiCam system was modified to image prompt gammas. A 1 cm thick continuous LYSO crystal was used and light collection was purposely limited to match the ASIC dynamic range which was designed for max. photon energy of 200 keV. This resulted in an approximate conversion gain of 5 photoelectrons per keV. A lead shielding was added to cover both the detection head and the electronic boards to minimize background detection during proton irradiation. The tungsten alloy collimator (16.96 g/cm3 with 90% W, 6% Ni and 4% Cu) was located half way at 15 cm from the beam axis, with 4 cm thickness, 63° slit angle, 6 mm slit width, 12 cm height. The collimator consisted of two blocks, each block being 16 cm in length along the beam axis.

These elements were positioned on a dedicated PMMA support. The camera and collimator were centred at the expected beam range depth at 100 or 160 MeV (6.7 and 15.2 cm respectively). The detector prototype has a limited useful field of view along beam axis, so it was translated along the beam axis by −40 mm and +40 mm to obtain a broader image when necessary. Measurements with a closed collimator were also realized by joining the right-angled faces of the two tungsten blocks (so that the slit width is 0 mm and the slit angle is) 90° resulting in a simple 4 cm thick tungsten wall. The number of protons delivered was recorded with a large parallel plate ionization chamber intercepting the beam.

Figure 13:
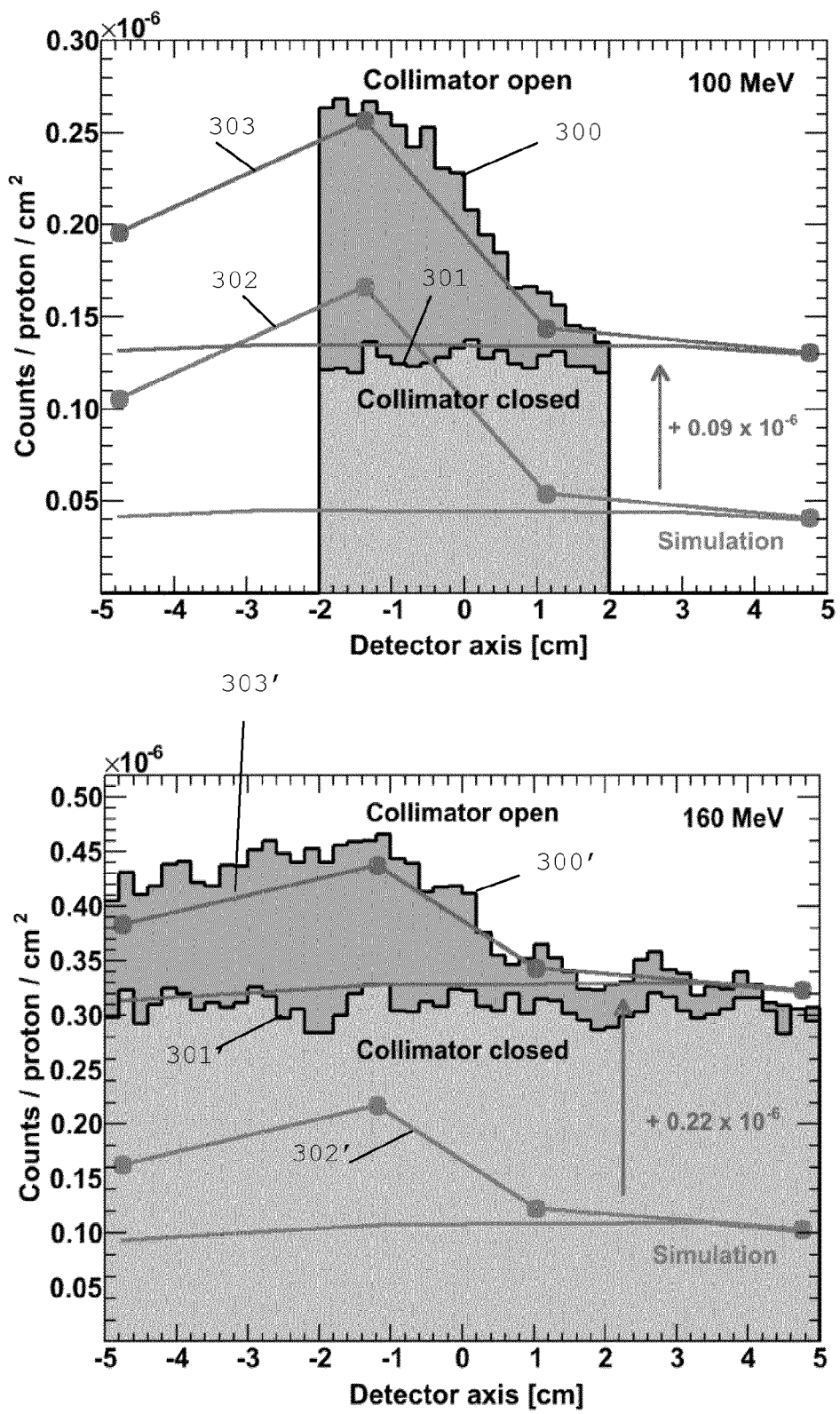
FIG. 13 shows detection profiles obtained with an experimental prototype of an apparatus according to the invention.

Measurements were realized with a continuous proton beam current of 40 pA at nozzle exit during 5 minutes at 100 MeV and 23 pA during 2 or 4 minutes at 160 MeV. These low current values, 100 times lower than maximum clinical values, were chosen in order not to saturate the HiCam system that was operated at 3500 counts/s. All measurements were corrected for the total dead time resulting from the 1 ms dead time after electronics reset every 5 ms and the 19.5 μs dead time after detection of an event. First acquisitions were realized without collimator for a homogeneous exposition of the camera and were used to correct further measurements. Profiles measured with the camera centred at the expected range depth for 100 and 160 MeV pencil beams are given in FIG. 13. Profiles obtained with the collimator open (6 mm slit width and 63° slit angle) are compared with closed collimator profiles (see curves 300/301 and 300'/301' respectively). The acquisitions at 100 MeV and 160 MeV were realized for $7.30 \times 10^{10}$ and $3.60 \times 10^{10}$ incident protons respectively, and were normalized per proton per steradian in FIG. 13. At 160 MeV, the HiCam system was translated by −40 and +40 mm to have a broader field of view. The 3-line segment curves 302 and 302' are obtained with a Monte Carlo simulation. These curves are shifted upwards in the graph towards the measured profiles, resulting in curves 303 and 303'. It can be observed that the characteristic peak and delta values of the measured profiles 300/300' are close to the predictions of the simulations as the opening difference contribution (difference between curves 300 and 301 for 100 MeV and between 300' and 301' for 160 MeV) is similar to the expected one. By applying the above-described method of determining the shift in the 3-line segment approximation, a shift in the beam range in the order of 1-2 mm can thus be detected.

Figure 14:
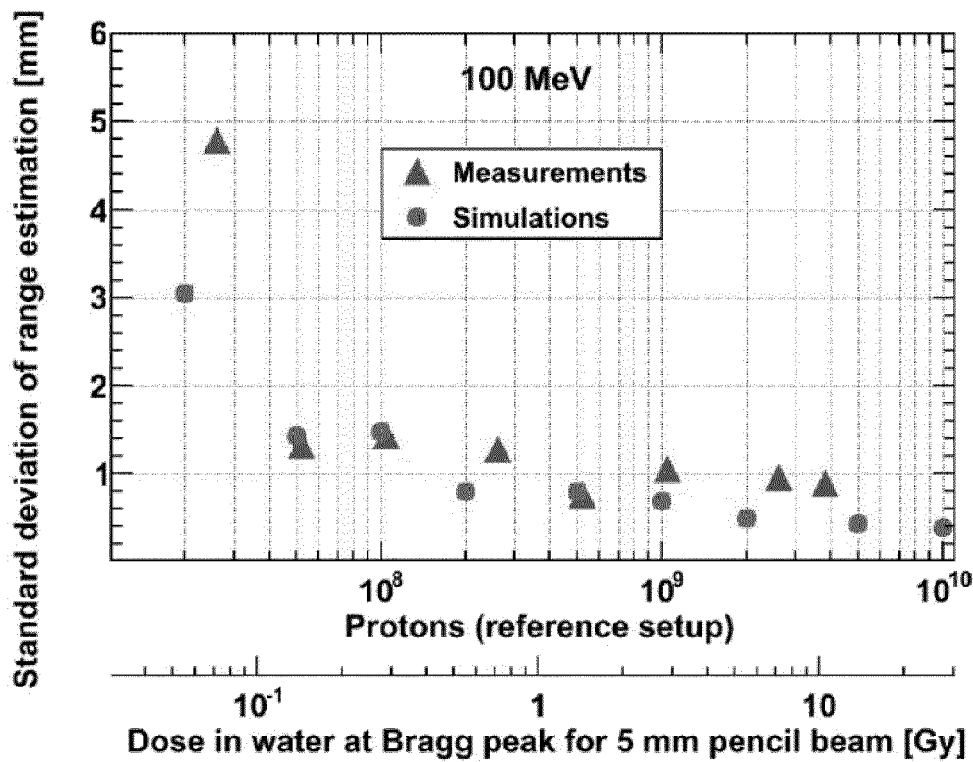
FIG. 14 shows the standard deviation of the difference between a measured and a real target shift, for proton beams of 100 MeV and 160 MeV, as a function of the number of incident protons.
Figure 14:
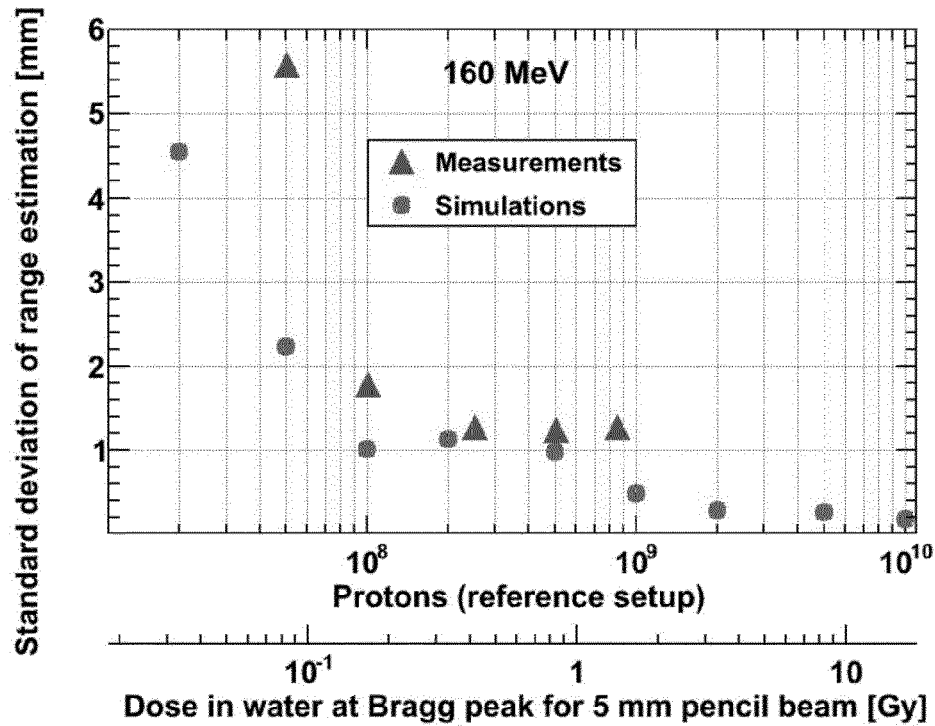

In order to test the accuracy of the apparatus, the target was moved along the beam axis, so that it looks like a range shift to the camera. The shift was estimated by measuring the shift of the 3-line segment fit, as shown in FIG. 12. FIG. 14 shows the standard deviation of the difference between measured target shift and the actual target shift, for proton beams of 100 MeV and 160 MeV, as a function of the number of protons in the proton beam. In order to evaluate the accuracy of the camera as a function of the number of incident protons, detection profiles were considered corresponding to different fractions of the total number of protons delivered. FIG. 14 shows that a slit camera equipped with a 20 cm high and 1 cm thick scintillator would achieve a 1-2 mm standard deviation on range estimation for number of incident protons that correspond to doses in water at Bragg peak as low as 14 cGy at 100 MeV and 17 cGy at 160 MeV for a pencil beam with a Gaussian profile of 5 mm sigma at target entrance.

The work leading to this invention has received funding from the European Union Seventh Framework Programme (FP7/2007-2013) under grant agreement n° 241851. One of the inventors of this invention obtained a funding as research fellow of Fonds de la Recherche Scientifique FNRS (Belgium).

The invention claimed is:

1. An apparatus for charged hadron therapy verification by detecting and/or quantifying prompt gammas produced when irradiating a target with a charged hadron beam, the beam being directed along a beam line, said apparatus comprising:
    a collimator formed of a first material and provided with a single slit-shaped portion which is open or which comprises a material of a lower thickness and/or density than said first material, said slit-shaped portion being configured to be arranged perpendicularly to the beam line and facing the target,
    a detection means suitable for detecting said prompt gammas, and
    a calculation and representation means,
    the slit-shaped portion is configured to allow the passage of prompt gammas emitted at least from a zone of the target corresponding to a portion of the beam line within said target, said portion of the beam line being considerably larger than the width of the slit-shaped portion, so that the slit shaped portion enables the detection of prompt gamma emitted not only from the direction which is at 90° with respect to the beam line,
    said detection means is configured to detect prompt gammas passing through the single slit-shaped portion, said prompt gammas being emitted from a plurality of locations within said zone of the target,
    said calculation and representation means is configured to derive from a detected prompt gamma a value representative of the dose at the location from where said prompt gamma is emitted, and to represent a dose-related distribution for said plurality of locations, thereby allowing to estimate the beam range within said target,
    said detection means and said calculation and representation means are configured to calculate and represent said value in a plurality of portions of said zone arranged along the beam line, to thereby obtain a one-dimensional view of the dose-related distribution within said zone.

2. The apparatus according to claim 1, wherein said detection means comprises a scintillator arranged at a distance from said slit-shaped portion, and having a surface facing said slit-shaped portion, and at least one array of photon counting devices associated with said scintillator.

3. The apparatus according to claim 2, wherein said scintillator is formed of a plurality of segments arranged in a row of segments oriented perpendicularly to the slit-shaped portion.

4. The apparatus according to claim 2, wherein said scintillator is formed of a plurality of segments arranged in a row of segments oriented in the direction of the thickness of said scintillator.

5. The apparatus according to claim 2, wherein said array of photon counting devices is arranged parallel to the scintillator.

6. The apparatus according to claim 2, wherein said array of photon counting devices is arranged laterally with respect to the scintillator and perpendicularly with respect to the slit-shaped portion.

7. The apparatus according to claim 2, wherein the scintillator material is LYSO or LSO.

8. The apparatus according to claim 2, wherein said scintillator and said array of photon counting devices are mounted inside a housing which is fixed with respect to the collimator.

9. The apparatus according to claim 1, wherein said slit-shaped portion comprises a solid material with a lower thickness and/or density than said first material.

10. The apparatus according to claim 1, wherein said slit-shaped portion extends between a front and a back plane of the collimator, said front plane being configured to face the target, and wherein the slit-shaped portion has two side walls, at least one of said two side walls diverging from a given narrower section of the slit-shaped portion to a broader section of the slit-shaped portion situated at the front plane of the collimator.

11. The apparatus according to claim 10, wherein the slit-shaped portion comprises a middle portion and two side portions, said side portions being located respectively between the middle portion and said front plane of the collimator, and between the middle portion and said back plane of the collimator, said side portions having diverging walls tapering outwards from the middle portion to the front, respectively the back plane of the collimator.

12. The apparatus according to claim 11, wherein the middle portion is a throat section having zero length, and wherein the detection means comprises a rectangular face placed at a distance (A) from the central longitudinal axis of the throat section, said face being furthermore symmetrical with respect to the plane through said central longitudinal axis and perpendicular to the plane of the throat section, and wherein the field-of-view angle ($\gamma$) is defined as the angle between said rectangular face of the detection means and a plane from the central longitudinal axis of the throat section to a side edge of the rectangular face, and wherein the angle ($\delta$) between the side walls of the side portion at the front of the collimator and the front plane of the collimator is between 80% and 100% of said field-of-view angle ($\gamma$).

13. The apparatus according to claim 11, wherein the width of the middle portion of the slit-shaped portion is between 1 and 10 mm.

14. The apparatus according to claim 1, wherein the thickness of the collimator is between 30 mm and 50 mm.

15. The apparatus according to claim 1, wherein the collimator material is tungsten or a tungsten alloy.

16. The apparatus according to claim 1, wherein the apparatus is configured to be movable with respect to the target.

17. The apparatus according to claim 16, further comprising a holder onto which the apparatus is mounted and a robotic arm onto which the holder is mounted.

18. The apparatus according to claim 1, wherein the collimator has the form of a flat panel provided with a longitudinal slit shaped portion.

19. The apparatus according to claim 1, wherein the collimator is cylindrically shaped, and configured to be placed around the target, and wherein the slit-shaped portion extends along a circular circumference of the collimator.

20. The apparatus according to claim 1, the apparatus further comprising means for approximating said one-dimensional view by a 3-line segment curve, wherein the means for approximating is configured to determine a shift of the 3-line segment curve with respect to a previously determined 3-line segment curve, or with respect to a simulated 3-line segment curve obtained from simulated data by which the apparatus is calibrated.

21. A method for charged hadron therapy verification by detecting and/or quantifying prompt gammas produced when irradiating a target with a charged hadron beam, said beam being directed along a beam line, comprising the steps of:
    arranging adjacent to a target a collimator with a single longitudinal slit shaped portion, said slit-shaped portion being configured to be arranged perpendicularly to the beam line and facing the target, said slit-shaped portion being configured to allow the passage of prompt gammas emitted at least from a zone of the target corresponding to a portion of the beam line within said target, said portion of the beam line being considerably larger than the width of the slit-shaped portion, so that the slit shaped portion enables the detection of prompt gamma emitted not only from the direction which is at 90° with respect to the beam line,
    irradiating said target with a charged hadron beam directed along said beam line,
    detecting prompt gammas emitted from a plurality of locations within said zone of the target, said prompt gammas passing through said single slit-shaped portion, and
    deriving from said detected prompt gamma a 1-dimensional dose-related distribution for said plurality of locations.

22. The method according to claim 21, wherein a window of energy levels for prompt gammas is defined, and wherein only prompt gammas are detected within said energy window.

23. The method according to claim 22, wherein said energy window is between 3 MeV and 7 MeV.

24. The method according to claim 22, wherein the energy window is between 3 MeV and 6 MeV.

25. The method according to claim 21, further comprising:
    estimating the beam range on the basis of said distribution.

26. The method according to claim 25, further comprising:
    approximating said distribution by a 3-line segment curve, and
    determining the shift of said curve with respect to a previously obtained 3-line segment curve.

27. The method according to claim 26, wherein the previously obtained 3-line segment curve is a curve obtained by the apparatus according to claim 1.

28. The method according to claim 26, wherein the previously obtained 3-line segment curve is a curve obtained from simulation data by which the apparatus according to claim 1 is calibrated.

29. An apparatus for charged hadron therapy verification by detecting and/or quantifying prompt gammas produced when irradiating a target with a charged hadron beam, the beam being directed along a beam line, the apparatus comprising:
- a collimator provided with a single slit-shaped portion, the slit-shaped portion being configured to be arranged perpendicularly to the beam line and facing the target,
- a detection means suitable for detecting the prompt gammas, and
- a calculation and representation means,
- wherein the slit-shaped portion is configured to allow the passage of prompt gammas emitted at least from a zone of the target corresponding to a portion of the beam line within the target, said portion of the beam line being considerably larger than the width of the slit-shaped portion, so that the slit shaped portion enables the detection of prompt gamma emitted not only from the direction which is at 90° with respect to the beam line,
- wherein the detection means is configured to detect prompt gammas passing through the slit-shaped portion, the prompt gammas being emitted from a plurality of locations within the zone of the target,
- wherein the calculation and representation means is configured to derive from a detected prompt gamma a value representative of the dose at the location from where the prompt gamma is emitted, and to represent a dose-related distribution for the plurality of locations, thereby allowing to estimate the beam range within the target,
- wherein the detection means and the calculation and representation means are configured to calculate and represent the value in a plurality of portions of the zone arranged along the beam line, to thereby obtain a one-dimensional view of the dose-related distribution within the zone,
- and wherein the apparatus is calibrated with simulated data so as to measure a shift in the beam range, said shift being measured with respect to a one-dimensional view of the dose-related distribution based on the simulated data.

30. A method for charged hadron therapy verification by detecting and/or quantifying prompt gammas produced when irradiating a target with a charged hadron beam, said beam being directed along a beam line, comprising the steps of:
- arranging adjacent to a target a collimator with a single longitudinal slit shaped portion, said slit-shaped portion being configured to be arranged perpendicularly to the beam line and facing the target, said slit-shaped portion being configured to allow the passage of prompt gammas emitted at least from a zone of the target corresponding to a portion of the beam line within said target, said portion of the beam line being considerably larger than the width of the slit-shaped portion, so that the slit shaped portion enables the detection of prompt gamma emitted not only from the direction which is at 90° with respect to the beam line,
- irradiating said target with a charged hadron beam directed along said beam line,
- detecting prompt gammas emitted from a plurality of locations within said zone of the target, said prompt gammas passing through said single slit-shaped portion,
- deriving from said detected prompt gamma a 1-dimensional dose-related distribution for said plurality of locations, and
- estimating the beam range on the basis of said distribution, by determining the shift of said 1-dimensional distribution with respect to a 1-dimensional distribution derived from simulated data.

* * * * *